United States Patent [19]
Blackledge

[11] 3,974,335
[45] Aug. 10, 1976

[54] HEARING TEST BY TELEPHONE INCLUDING RECORDED RESULTS

[75] Inventor: Vernon O. Blackledge, Scottsdale, Ariz.

[73] Assignee: Richard Besserman, Scottsdale, Ariz.

[22] Filed: June 6, 1974

[21] Appl. No.: 476,884

[52] U.S. Cl. .................................. 179/1 N; 179/6 R
[51] Int. Cl.² ......................................... H04R 29/00
[58] Field of Search ................. 179/6 R, 6 AC, 6 E, 179/1 N, 100.1 R, 100.1 DR

[56] References Cited
UNITED STATES PATENTS

| | | | |
|---|---|---|---|
| 3,392,241 | 7/1968 | Weiss et al. ......................... | 179/1 N |
| 3,808,354 | 4/1974 | Feezor et al. ........................ | 179/1 N |
| 3,809,811 | 5/1974 | Delisle et al. ........................ | 179/1 N |
| 3,810,316 | 5/1974 | Lahlou ................................. | 179/6 E |

Primary Examiner—Raymond F. Cardillo, Jr.
Attorney, Agent, or Firm—Cahill, Sutton & Thomas

[57] ABSTRACT

A system for testing the hearing of a patient by telephone is disclosed. The patient calls a number, either by touch tone or by dialing, whichever is available, that gives access to the testing equipment. The equipment gives the patient instructions as to how to proceed. The equipment, during the course of the test, applies discrete audio tones at various levels to the phone that the patient is holding to one ear, and records the tones and levels that the patient can hear. The process is repeated for the other ear and this is also recorded. A code number is also recorded so that the test results may be recovered. When the test is complete, the equipment tells the patient what the code number is and that upon payment of a fee the results of the test will be transmitted to him. The equipment may be used in a doctor's or personnel officer's office, in which case the equipment gives the code number, but does not mention a fee.

9 Claims, 3 Drawing Figures

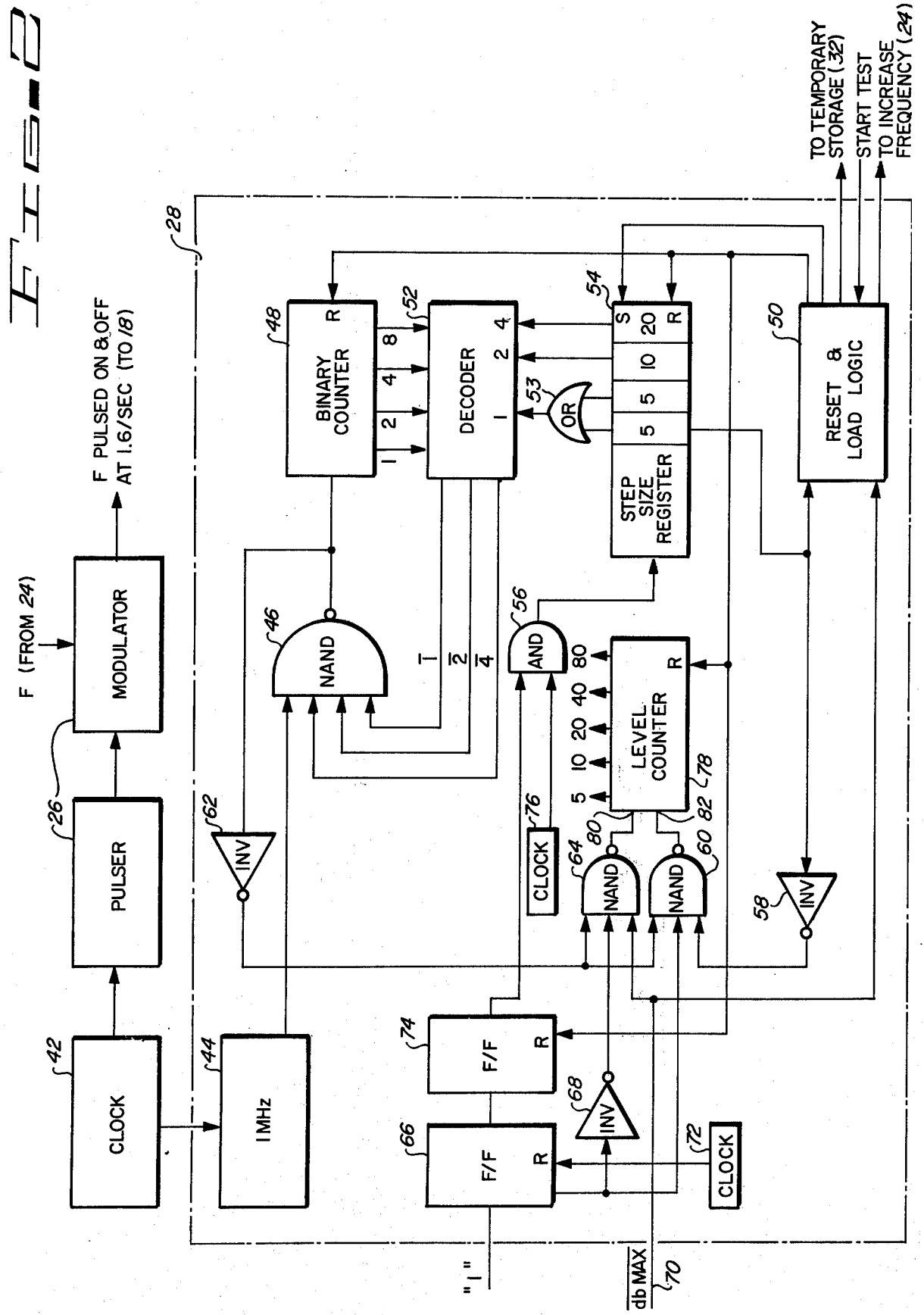

HEARING TEST BY TELEPHONE INCLUDING RECORDED RESULTS

The present invention relates to hearing testing devices, and more specifically, to centralized apparatus which may be reached by calling a telephone number from any phone for testing the hearing of the caller or patient. The apparatus stores the information and informs the patient how he or she may obtain the results of his hearing test.

BACKGROUND OF THE INVENTION

Hearing test devices are known. The such known devices are usually located in a hearing specialist's office, whereby a trip to the office is required if the hearing of the patient is to be tested. Furthermore, a skilled operator is required to apply the test to the patient and to interpret the test results, whereby the hearing test is usually expensive. Hearing screening apparatus is also known. The hearing screening apparatus differs from the hearing testing equipment in that the hearing screening equipment merely checks the hearing of the patient to determine if his hearing passes, that is, is good enough to satisfy the requirements of a particular situation, such as employment, and does not give a profile of the patient's hearing ability over the normal hearing range. The hearing screener needs no skilled attendant, but is usually in an office to which the patient or applicant for employment must go.

SUMMARY OF THE INVENTION

It is an object of this invention to provide improved hearing testing equipment.

It is a further object of this invention to provide an apparatus for testing the hearing of a patient who is at a remote point from the apparatus.

It is still a further object of this invention to provide a remotely positioned apparatus for testing hearing which records the hearing profile of the patient and informs the patient how to obtain his hearing profile.

In accordance with the invention, the patient calls a telephone number, either by touch tone or dialing apparatus, whichever is available. The ring signal is received at a test controlling portion of the apparatus. The test controller operates a relay which answers the telephone line and starts a tape player. The tape player is connected to the telephone line and the instructions recorded thereon are heard by the patient.

As a sample of the instruction, the patient may be told to dial (in this specification, the word "dial" includes dialing or touching a tone button of a telephone) a number such as "3" if the patient did not understand the instructions and wishes a repeat, or he may dial a "1" if he wishes to continue the test. Of course, the patient may hang up (put the receiver back on the hook) if he so desires, and redial. If the patient makes no answer, the apparatus waits a reasonable time, such as 20 seconds, and hangs up. If a 1 is dialed by the patient, a predetermined frequency $f_1$ at a predetermined level, preferably at 20 dB, is applied to the line. This frequency is pulsed on and off at a suitable rate, such as 1.6 times per second. The equipment that produces the tone is set up to produce an intensity, for all frequencies, such that, when a particular frequency is applied to the patient's ear, losses in the test equipment as well as losses in the telephone equipment are compensated for, so that the test is a realistic one. The pulsed signal is applied for an appropriate time, such as five seconds on and five seconds off. If the signal is heard, the patient dials a 1. If no 1 is received by the machine in convenient time, i.e., 5 seconds, the intensity is increased by a relatively large step. If the patient does not respond, the intensity is increased again by another relatively large step until either the patient responds or the maximum signal that the apparatus is capable of producing is reached. If still no response is made by the patient, this fact is recorded and the apparatus sends out another frequency $f_2$ at about 20 dB over the normal level for that frequency $f_2$.

If, however, after the first or subsequent increase in level of the sound at frequency $f_1$, the patient dials a 1, the apparatus sends out the frequency $f_1$ at a reduced intensity, preferably an intensity halfway between the intensity last sent (which elicited a response) and the previous intensity (which did not produce a response). If no response is received from the patient, the level is increased, preferably to a point about halfway to the level that was heard. If a response is received, the level is decreased still more, approaching the last large step level that was not heard. In this way, the hearing of the patient at frequency $f_1$ is bracketed in levels. The lowest level of hearing is recorded.

The same procedure is followed with $f_2$ and $f_3$ and so forth, usually for seven frequencies in all, for the same ear. In each case, if there is a hearing loss, the lowest level that is heard which brackets the hearing ability of the patient is temporarily recorded by the inventive equipment. When the hearing test of the one ear is completed by the apparatus, the test is stopped and the patient is asked to validate the test by dialing a 1. If he does not, the apparatus hangs up. If he does so, the test results are recorded on a permanent record, usually on a tape. The apparatus tells the patient to apply the receiver to the other ear, and the test is repeated, bracketing the hearing again by using the described method, and the test for the other ear is permanently recorded on the tape upon the patient validating the procedure by dialing a 1.

Now the patient is given instructions as to how he can obtain the results of his hearing tests. This is done by another tape recorder. This recorder tells the patient to get a pencil, write down an address, and send money to the address. If the patient dials a 3, this part of the instructions is repeated. If the patient dials a 1, a further tape recording is applied, both to the phone and to the record of the patient's hearing test; this last mentioned number, which may be a composite of digits and letters, being the code for identification of the patient's hearing test. The patient is told to send his money and request for his hearing test and this code number to a particular address. After the code number is given to the patient, the apparatus "hangs up" the receiver and is ready for another testing operation.

If the testing is done in such a manner that individual payments are not made, such as where the apparatus is leased by a doctor or an employment office, the instructions given the patient are modified to the point that no address and no request for payment is made, but a code number is supplied the doctor or the employment office.

BRIEF DESCRIPTION OF THE DRAWINGS

The invention will be better understood upon reading the following description in connection with the accompanying drawings wherein:

FIG. 2 is a block diagram of the level logic of FIG. 1 and including further elements.

DESCRIPTION OF A PREFERRED EMBODIMENT

Figure 1:
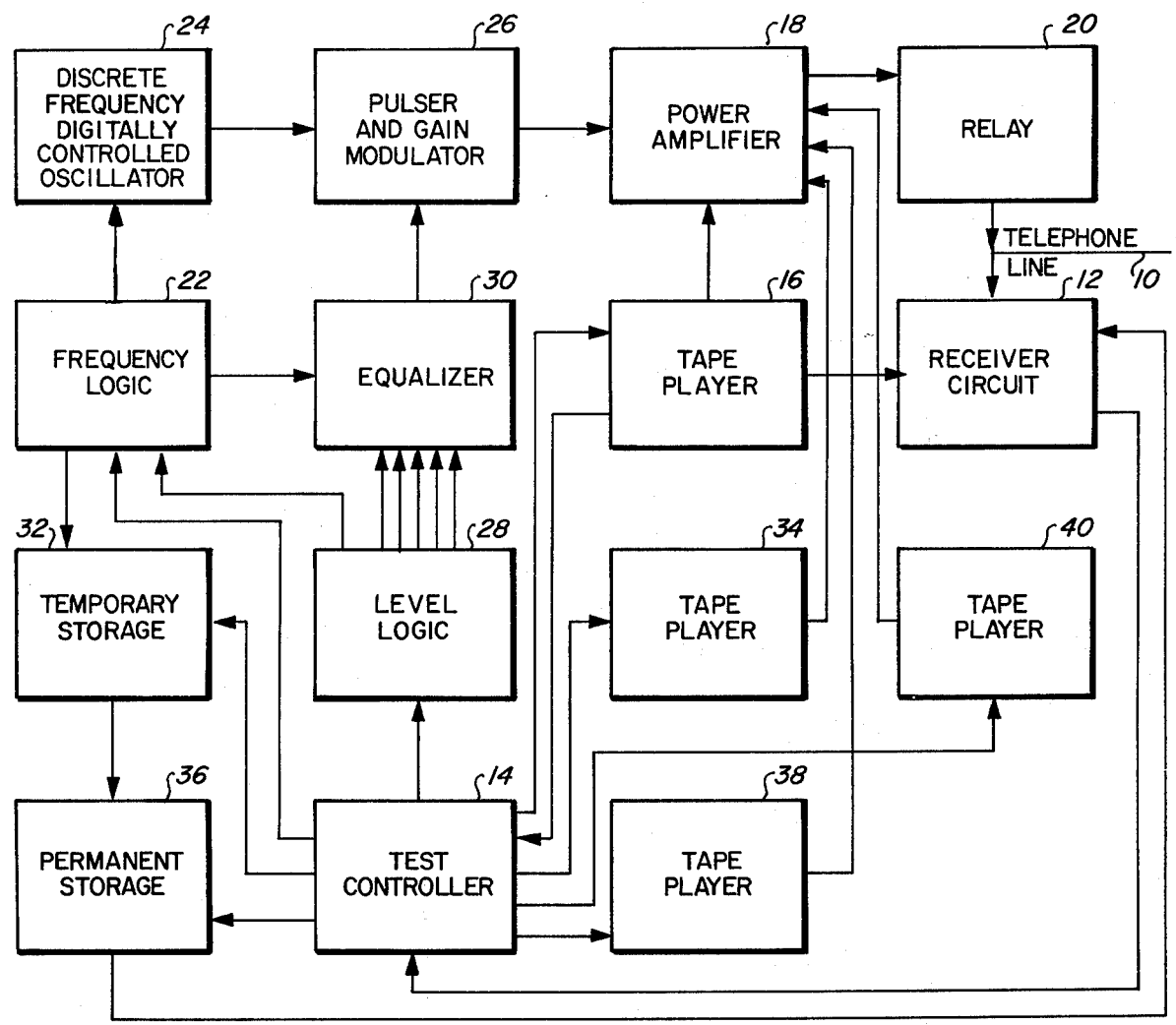
FIG. 1 is a block diagram of the remotely positioned hearing test apparatus of this invention.

A patient, not shown, is positioned at a telephone at a place remote from the apparatus of FIG. 1. He picks up his phone and dials (or touch tones) the number to which the telephone line 10 is connected. The ringing portion of the signal arrives at a receiver circuit 12 and goes from there to a test controller 14. The test controller 14 is connected to a first tape player 16, which is connected by way of a power amplifier 18 and a relay 20 to the telephone line 10. The tape player 16 is started, whereby the patient is given instructions and is requested to dial a 3 if he wishes a repeat of the instructions or a 1 if he wishes the test to continue. The patient, of course, may hang up if he so desires and redial the number. If a 3 is received by the apparatus, the tape in the player 16 is rewound and the instructions are repeated. If a continuous tape loop is used, no rewind is necessary. If a 1 is received, the test continues as explained below. If there is no answer in a reasonable period, such as 20 seconds, the apparatus hangs up.

If a 1 is received, the test continues. The test controller 14 is connected to a frequency logic circuit 22 which is in turn connected to a digitally controlled oscillator 24 which is connected through a pulser and gain modulator 26 to the power amplifier 18. The frequency logic 22 applies a digital word to the oscillator 24 to cause it to produce an audio tone at a frequency $f_1$. The pulser 26 modulates the signal applied to it with a suitable wave form (preferably a triangle wave) so that the frequency $f_1$ is turned on and off at a rate of 1.6 times per second. The test controller 14 is also connected to a level logic circuit 28. The level logic circuit 28 is connected to the frequency logic 22 and to an equalizer 30. The frequency logic 22 is also connected to the equalizer 30 and the equalizer 30 is connected to the pulser 26. The result is that the wave at frequency $f_1$ is applied, by way of the power amplifier 18 and the relay 20, to the telephone line 10 in a modulated form, and at an intensity or volume such that the volume at the patient's telephone (not shown) is a known value, after the losses in the line and equipment are allowed for. It will be noted that the frequency logic 22 is connected to temporary storage equipment 32 and that the test controller 14 is also connected to the temporary storage 32. Therefore, the digital word applied to the digitally controlled oscillator 24, which represents the frequency thereof, is connected to the temporary storage 32 and is recorded thereon.

The patient's instructions are to dial 1 if he hears a tone. If he dials 1, the test controller is notified by way of the receiver 12, and the test controller 14 applies a voltage to the temporary storage 32 to cause it to record an indication that the patient heard the frequency $f_1$ at its initial level, which is usually above the normally lowest heard intensity for a wave of frequency $f_1$. As will be more fully explained hereinbelow in connection with FIGS. 2 and 3, the volume of the frequency $f_1$ is made to go up and down as necessary to bracket the hearing ability of the patient over a small range, such as 5 dB, and the last volume of frequency $f_1$ that is heard is recorded. The test controller 14 then causes a frequency $f_2$ to be applied to the line 10 due to the interconnection of the test controller 14, the logic level 28, the equalizer 30, the frequency logic 22, the digitally controller oscillator 24 and the pulser 26, at the initial volume level and the process is repeated.

Let it be assumed that the patient did not dial 1 when the frequency $f_1$ at its initial level was applied to his ear. The test controller 14, after waiting a reasonable time, such as 5 seconds, by means of the connections noted above, causes the equalizer 30, the oscillator 24 and the pulser 26 to apply the wave $f_1$ at a higher level, say twenty dB higher at the patient's ear, to the line 10. If the patient dials 1, the patient heard this intensity level but (perhaps) could have heard a lower level. So the test controller 14 causes the pulser 26 to send out the frequency $f_1$ at a level between the initial level and the 20 dB higher level, such as 10 dB above the initial level. If the patient sends back a second 1, then he might have heard a five dB lower level at his phone, so the controller sends out the frequency $f_1$ at this five dB lower level. If the patient sends back a third 1, his hearing is bracketed as between the level he heard and five dB lower level.

As will be explained more fully hereinbelow, until the patient sends back his first acknowledgement of any frequency (by dialing a 1) the level of the wave is increased by large steps of about 20 dB, for example. Then the frequency is not changed, but the intensity is decreased by 10 dB, for example. If the patient responds, the intensity is decreased by 5 dB. If he does not respond, the intensity is increased by 5 dB. The final result is that for each frequency of the several, seven in a preferred embodiment, the hearing ability of the patient is bracketed in a range of 5 dB. The temporary storage 32 stores all frequencies applied to the line 1 and all responses (if any) made by the patient. Of course, it is possible that the patient may not hear one or more test frequencies at the highest level within the capabilities of the machine, in which case this is stored in the temporary storage 32.

If it is desired to bracket the patient's hearing to within a two and one-half dB range, further equipment may be added. Any numbers used herein are examples only and not limiting.

As noted, when the patient's hearing has been tested for frequency $f_1$, the test is made for frequency $f_2$ at or above the appropriate normal intensity and if there is no response, the hearing of the patient is bracketed (if he hears $f_2$ at all). Then the patient's hearing is tested at $f_3$, and so forth, for as many frequencies, seven usually, to produce a hearing profile for the patient.

After the patient has had his hearing tested in one ear for the seven frequencies, he is asked to validate by dialing a 1. If the 1 is not received, the apparatus hangs up. However, if a 1 is received, a tape player 34 tells the patient to put the phone at his other ear and to dial 1 when this is done so that the testing of the other ear can proceed. A separate tape player 34 is used for this purpose so that the tape player 16 is used only for giving instructions for initiating the test and for testing one ear. This test of the other ear is exactly like the test for the first ear.

Then, when all the tests are complete, the test controller 14 causes another tape player 38 to get on the line and tell the patient to get pencil and paper and take down instructions as to how to obtain the results of the test, that is, whom to write and how much money to send. If the patient wants a repeat, he dials 3. If he hears sufficiently to take down the instructions by the player 38, he dials a 1. This 1 causes a test number counter to advance (located in temporary storage 32). This test number and the right ear data are then recorded in permanent storage 36. A tape player 40 then plays just long enough to give the next code number, of the plurality thereof recorded therein, and this code number not only goes to the patient, but is the same test number that is simultaneously recorded on the permanent storage 36, to identify that patient's hearing profile. Each tape player 16, 34 and 38 has an instruction message thereon for its own part of the process, as noted above, and the tape player 40 has thereon successive code numbers which may be renewed when all have been used. After the tape player 40 has given its code number, it causes hang-ups of the apparatus so that another patient may have his hearing tested and his hearing profile provided. Whenever a hang-up occurs, the temporary storage 32 is cleared and the tape players 16, 34 and 38 are ready to repeat their messages. The permanent storage 36 is retained until used or until a reasonable time has expired. Or, if desired, the permanent storage may be retained indefinitely.

If the apparatus is under lease, whereby no individual payment is requested, the player 38 may be omitted and the code number is given by tape player 40 when the test is completed.

The logic level 28 of FIG. 1 is shown in more detail in FIG. 2. A clock 42, which is not part of the logic level 28, applied a square wave which is on for five seconds and off for five seconds to a one megahertz oscillator 44. The output of the oscillator 44 is applied to one input of a negative and, or NAND, circuit 46. As is known, when a high is applied to all the inputs of a NAND circuit, a low appears on the output thereof, otherwise the output of the NAND remains high. In this description, "high" or "positive" are used synonymously and "low" or "negative" as the opposite to either "high" or "positive." The output of the NAND 46 is applied to a binary counter 48. As is known, the several outputs of a binary counter are high or low, to indicate a "one" or "zero" in the binary code of numbers. The left output indicates a one or zero. The next-to-left output indicates a two or zero, as shown, and so forth. The counter 48 is set at zero by application of a pulse from a reset and load logic 50 applied to the R terminal of the counter 48. The four outputs of the counter 48 are connected to inputs of a decoder 52 which notes the voltage at the outputs of the binary counter 48. As noted below, the decoder 52 puts any appropriate voltage on respective other inputs of the NAND 46 under control of a step size register 54.

The reset and load logic 50 applies a start pulse to the S connection of the section marked 20 (or the 20 section) of the step register 54. This pulse is stepped to the left one step at a time upon application of a pulse to the input thereof from an AND circuit 56, as will be further explained. After a test, the reset logic 50 applies a pulse to the R input of the register 54 to clear it of pulses and to be ready to have a pulse put into the 20 section at the start of the next test. It will be noted that the step register 54 has, besides the 20 section, a 10 section and two 5 sections. The 20 and the 10 sections are connected to the decoder 52 by individual connections, while the two 5 sections are connected via an OR gate 53 to an individual input of the decoder 52. The second 5 section is connected to the reset logic 50 and through an inverter 58 to a connection of a NAND 60.

The output of the NAND 46 is connected by way of an inverter 62 to individual inputs of the NAND 60 and another NAND 64. A third input of the NAND 60 is connected to the output of a flip-flop circuit (hereinafter F/F) 66 whose input is connected to the telephone line 10 by way of the receiver circuit 12 of FIG. 1. The F/F 66 is also connected by way of an inverter 68 to a second input of the NAND 64. The third input of the NAND 64 is connected to a connection 70 labelled $\overline{dB}$ Max that indicates when the maximum volume is being applied to the patient's ear. The connection 70 is also connected to the reset and load logic 50 for a purpose to be disclosed.

A clock 72, which may be the clock 42 if desired, is connected to the R terminal of the F/F 66 to reset it, after each intensity level of a wave is applied to the ear of a patient. The output of the F/F 66 is connected to a F/F 74 and the output of the F/F 74 is connected to one input of the AND 56, to the other input of which a clock 76 is connected.

The outputs of the NANDs 60 and 64 are connected to inputs 82 and 80 respectively of a level counter 78, a reset voltage being applied to the R input of the level counter 78 by the reset logic 50 as shown. The counter 78 is a well known device that will count up if a low voltage is applied to its up input 80 and will count down if a low voltage is applied to its down input 82. The level counter has several outputs marked 5, 10, 20, 40 and 80, and these outputs are connected to the equalizer 30 of FIG. 1 to cause it to apply different volumes to the pulser and gain modulator 26. Counter 78 is known in the art as an up-down counter. Counter 78 has a plurality of fixed value output corresponding to preselected audio signal intensities as noted. Counter 78 is caused to count up in response to a first voltage signal. Each audio signal intensity is actuated successively in response to each first voltage signal to cause a successive increase in the intensity of said tone when no response is applied to the apparatus within the predetermined time. Counter 78 is caused to count down in response to a second voltage signal. Each audio signal intensity is actuated successively in response to each second voltage signal to cause a successive decrease in the intensity of the tone when the patient signals that he heard the tone. This process is more fully described hereinbelow as a part of the operation of the system.

Having described the level logic 28 of FIG. 1, operation of the device of this FIG. will be described in connection with FIG. 3. In the first place, it is assumed that the patient's hearing is impaired. Therefore, the first volume of sound at each frequency that is applied to the patient's ear is at the level of 20 dB above the normal hearing threshold for that frequency. Let us assume the first patient has normal hearing. The level of the sound applied to the first patient's ear (at the first test frequency $f_1$) is indicated by the line A of FIG. 3. Since the patient hears the sound, he will dial a 1 in the time interval between the first two vertical dotted lines, say 5 seconds. The 1 will cause the F/F 66 to flip, that is, change its state of output voltage and this will cause the F/F 74 to flip, applying a high to one input of the NAND 56. F/F 74 remains flipped, once it has been flipped, until the test with a particular frequency, such as $f_1$, is completed. The clock 76 applies a high to the other input of the AND 56 and a high is applied to the input of the step size register 54, and the pulse which has been put into the 20 portion of the step register 54 moves to the 10 portion thereof, whereby the 10 section of the step register 54 applied a logical one to decoder 52.

No pulse from pulser 44 passes the NAND 46 unless all four inputs thereof are positive. The binary counter 48 counts only the pulses that pass the NAND 46. The binary counter 48, the decoder 52, and the NAND 46 count 4, 2, or 1, depending on which input to the decoder 52 that is connected to the step register 54 has a high thereon. It is desired to count two (each count represents 5 dB), since the 10 section of the register 54 has a pulse in it. A positive is applied to the corresponding inputs of the NAND 46 and pulses from pulser 44 are passed by the NAND 46 to the counter 48 until the binary counter counts two. Then at least one of the inputs of the NAND 46 becomes negative and counting stops. The two pulses that passed the NAND 46 are applied to the inverter 62 where they are again inverted. These positive pulses are applied to both NANDS 64 and 60. Since dB maximum has not been reached, the third input of NAND 64 is positive. Since a 1 has been received by the F/F 66, a low is applied to the middle input of NAND 64 and there is no output of NAND 64 and level counter 78 does not count up. As for NAND 60, all three of its inputs are high, the top one when pulses pass the NAND 46, the middle one since the 1 has been received, and the lowest one since the pulse in register 54 is not in the left-hand 5 section of the step register 54. The level counter 78 has input applied to its countdown terminal 82 and it counts down to the 10 dB level shown at the top of level counter 78 and in FIG. 3, and a sound at the same frequency and at the (resultant) 10 dB level is applied to the ear of the patient for the next time period.

We have assumed that the patient's hearing is normal at this frequency, so he hears the 10 dB sound and he dials a 1. The F/F 74 in cooperation with the clock 76 and the AND 56 causes a pulse to be applied to the step register 54 and the pulse therein is stepped to the right-hand 5 section, and now the counter 48 counts one and one pulse is applied to the countdown input 82 of the level counter 78 and the sound goes down to 5 dB above normal. The patient hears and dials 1 and the pulse in the step register 54 goes to the left-hand 5 section. The connection of the left-hand 5 section by way of the inverter 58 to the NAND 60 applies a negative to the level counter 78 and the level counter 78 can neither count up nor down. It is now known that at the first frequency the patient hears a sound of 5 dB. He may hear at lower than 5 dB, so his hearing is bracketed between 5 dB and the normal or 0 dB. The left-hand 5 section is also connected to the reset and load logic 50 as shown and it is recorded in the temporary storage that the patient can hear 5 dB sound, and the equipment is reset and frequency $f_2$ will be applied to the patient's ear.

Figure 3:
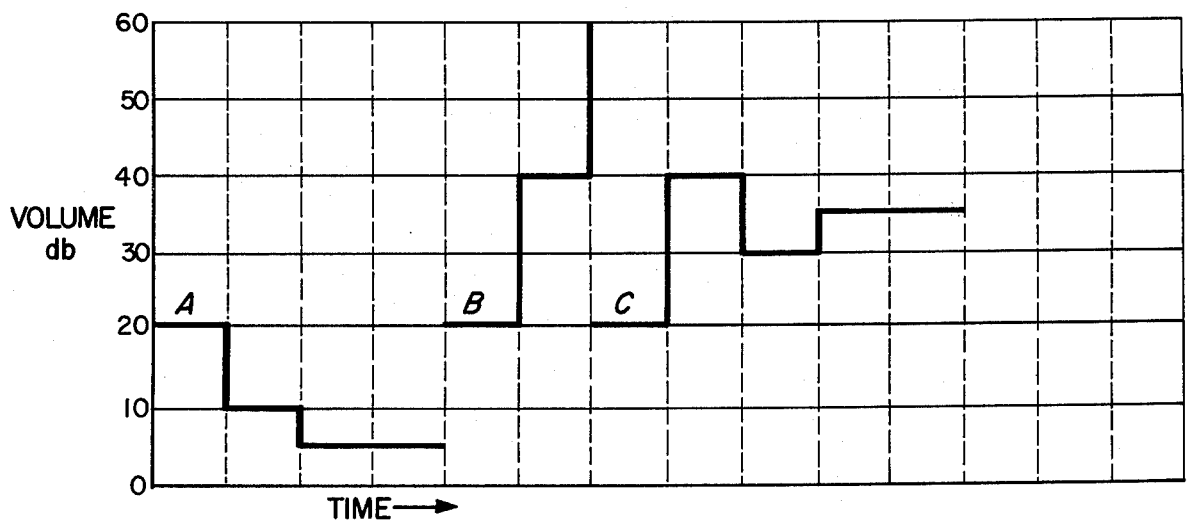
FIG. 3 is a diagram useful in explaining the operation of this preferred embodiment of the invention.

Let us now assume that the patient cannot hear the original 20 dB sound, see curve B or FIG. 3. Since no 1 is dialed during the first portion of this test, neither F/F 66 or 74 is activated, and no pulse is applied from the AND 56 to the step register 54, whereby the original pulse stays in the 20 section and the counter 48 counts four before the NAND 46 is blocked. These four pulses are applied as highs to the two NANDS 64 and 60. Since there is no 1, a low or negative is applied to the middle input to NAND 60, disabling it, but a positive is applied to the middle input of NAND 64. Since dB max has not been reached, that is, since the maximum sound that the equipment is capable of has not been reached, a positive is applied to the lower input of NAND 64 and from there to the countup input 80 of level counter 78 and the counter 78 counts up to 40 dB. If the patient still cannot hear, no 1 is dialed, the counter 48 counts four more and the counter 78 counts up four more and sends out the maximum sound, such as 80 dB, that the apparatus is capable of. If there is still no 1, the NAND 64 is disabled by the negative applied from dB max to NAND 64 and the reset and load logic 50 gets the signal and records the fact that at this frequency the patient's hearing level is at least as high at dB max (the loudest sound the apparatus is capable of at this frequency).

Now let us assume the patient can hear 40 dB but cannot hear 20 dB, see curve C. When the patient hears at line 40 dB, he dials a 1 which causes F/Fs 66 and 74 to flip and causes AND 56 to step the pulse from the 20 section to the 10 section of the step register 54. Binary counter 48 counts two. Since the 1 was received, level counter 78 counts down 10 dB. Let us assume the patient did not hear this 30 dB level. F/F 74 stays flipped and at the next pulse of clock 76, the AND 56 causes the pulse in register 54 to go to the right-hand 5 section, whereby counter 48 counts one. Since no 1 was dialed, the counter 78 counts up one, and sound at 35 dB is applied to his ear. If the patient hears, and dials 1, the operation of the left-hand section of 5 section and inverter 58 prevents the level counter 78 from counting down and the patient's hearing is between 30 and 35 dB at that frequency.

In each case, if the patient hears at all, the patient's hearing is recorded and it is known that he hears between the recorded level and 5 dB lower, bracketing his hearing and recording a profile of his hearing.

The bracketing of the patient's hearing using 20, 10 and 5 decibel steps as explained above may be changed to another bracketing procedure using, for example, 20, 20, 10, 10, and 5, 5, 5 decibel steps by appropriate coupling of the step register 54 to the decoder 52.

In the drawings, rectangles are used to show conventional elements. Telephone answering apparatus are well known and so are devices for applying tones to lines at successive amplitudes, and so are permanent and temporary storage devices and tape players that must be rewound to replay or that use endless tapes that play the message each time the tape is played for its full circumference. Therefore, the claims are not to be limited by the above descriptions or by the drawings, but only as necessitated by the appended claims.

What is claimed is:

1. Means for providing a hearing profile from a remote point including a line over which audio signals may be passed, comprising,
    a. means to send hearing test directions over said line to a patient;
    b. means to send a tone of audio frequency over said line at a first intensity;
    c. means to increase the intensity of said tone when no response is applied to said apparatus after a predetermined time;

d. means responsive to the patient's signal that he heard the tone to decrease the intensity of the tone;
e. said means to increase and to decrease the intensity of said tone including an up-down counter;
f. said counter having a plurality of fixed value outputs corresponding to preselected audio signal intensities;
g. means to cause said counter to count up in response to a first voltage signal, each said audio signal intensity being actuated successively in response to each first voltage signal to cause a successive increase in the intensity of said tone when no response is applied to said apparatus within said predetermined time and to count down in response to a second voltage signal, each said audio signal intensity being actuated successively in response to each second voltage signal to cause a successive decrease in the intensity of said tone when said patient signals that he heard the tone;
h. means to apply a tone of a different audio frequency over said line at different intensities;
i. means to record the frequencies and intensities thereof and the responses made thereto by the patient, whereby a hearing profile is produced;
j. means to instruct the patient where to send for his hearing profile, and
k. means to send the patient and to record on said profile a code number identifying the profile.

2. The invention of claim 1 in which means are provided to repeat said bracketing procedure for a tone of a different frequency in the case of a large loss of hearing.

3. The invention as expressed in claim 1 in which the increased intensity is of a relatively large value and means are provided to decrease the intensity of the tone of said increased signal by a different step size upon receipt of the patient's signal.

4. The invention as expressed in claim 3 in which the intensity is increased by a different step size upon failure to receive a patient's signal that he heard a decreased signal, whereby the patient's hearing level is bracketed.

5. Means for bracketing the hearing ability of a patient which comprises,
a. means for applying a tone at an audio frequency to a sound-producing device which may be applied to a patient's ear at a predetermined intensity;
b. means to indicate that the patient heard the tone;
c. means responsive to said indicating means to decrease the intensity of said tone by a programmable step size;
d. means to increase said decreased intensity responsive to lack of indication by a programmable step size;
e. said means to increase and to decrease the intensity of said tone including an up-down counter; and
f. means to cause said counter to count up in response to a first voltage signal, each said audio signal intensity being actuated successively in response to each first voltage signal to cause a successive increase in the intensity of said tone responsive to said lack of indication when no response is applied to said apparatus within said predetermined time and to cause said counter to count down in response to a second voltage signal, each said audio signal intensity being actuated successively in response to each second voltage signal to cause a successive decrease in the intensity of said tone when said patient signals that he heard the tone.

6. The invention as expressed in claim 5 in which said predetermined intensity is above the hearing threshold for a normal ear.

7. The invention as expressed in claim 5 in which means are provided to increase the intensity of said tone in steps until a maximum intensity is reached responsive to lack of indication that said tone has been heard.

8. The invention of claim 5 in which means are provided to prevent counting down by said first counter more than once by the same small amount.

9. The invention of claim 8 in which means are provided to repeat said bracketing procedure for a tone of a different frequency in response to applying said maximum intensity to said sound-producing device.

* * * * *

UNITED STATES PATENT AND TRADEMARK OFFICE
Certificate

Patent No. 3,974,335                      Patented August 10, 1976
Vernon O. Blackledge Application having been made by Vernon O. Blackledge, the inventor named in the patent above identified, for the issuance of a certificate under the provisions of Title 35, Section 256, of the United States Code, adding the name of Richard Besserman as a joint inventor, and a showing and proof of facts satisfying the requirements of the said section having been submitted, it is this 18th day of March 1980, certified that the name of the said Richard Besserman is hereby added to the said patent as a joint inventor with the said Vernon O. Blackledge.

FRED W. SHERLING,
*Associate Solicitor.*